United States Patent
Borchardt

(10) Patent No.: US 10,918,995 B2
(45) Date of Patent: Feb. 16, 2021

(54) DEVICE FOR MASS TRANSFER, AND METHOD OF PRODUCTION

(71) Applicant: enmodes GmbH, Aachen (DE)

(72) Inventor: Ralf Borchardt, Aachen (DE)

(73) Assignee: enmodes GmbH, Aachen (DE)

(*) Notice: Subject to any disclaimer, the term of this patent is extended or adjusted under 35 U.S.C. 154(b) by 186 days.

(21) Appl. No.: 16/089,212

(22) PCT Filed: Mar. 29, 2017

(86) PCT No.: PCT/EP2017/000377
§ 371 (c)(1),
(2) Date: Sep. 27, 2018

(87) PCT Pub. No.: WO2017/167443
PCT Pub. Date: Oct. 5, 2017

(65) Prior Publication Data
US 2019/0126205 A1    May 2, 2019

(30) Foreign Application Priority Data
Mar. 29, 2016 (DE) .................. 10 2016 003 611

(51) Int. Cl.
*A61M 1/16*      (2006.01)
*B01D 63/02*     (2006.01)

(52) U.S. Cl.
CPC .......... *B01D 63/021* (2013.01); *A61M 1/1621* (2014.02); *A61M 1/1698* (2013.01); *B01D 63/02* (2013.01); *B01D 2323/42* (2013.01)

(58) Field of Classification Search
CPC .... B01D 63/02; B01D 63/021; B01D 63/022; B01D 63/024; B01D 2313/08;
(Continued)

(56) References Cited

U.S. PATENT DOCUMENTS

| | | | | |
|---|---|---|---|---|
| 4,770,778 A | * | 9/1988 | Yokoyama | B01D 63/022 210/321.69 |
| 4,940,617 A | * | 7/1990 | Baurmeister | B01D 63/02 428/113 |

(Continued)

FOREIGN PATENT DOCUMENTS

| | | |
|---|---|---|
| DE | 28 25 065 A1 | 12/1979 |
| EP | 0 285 812 A1 | 10/1988 |

(Continued)

OTHER PUBLICATIONS

English language machine translation of JPH01176405, 4 Pages, No Date.*

(Continued)

*Primary Examiner* — Pranav N Patel
(74) *Attorney, Agent, or Firm* — Norris McLaughlin, P.A.

(57) ABSTRACT

A device for mass transfer between blood and a transfer medium, in particular a gas/gas mixture, includes a chamber through which blood can flow and in which a plurality of mass-permeable hollow fibers of at least one hollow fiber mat, in which the hollow fibers are held at a spacing by way of warp threads, are disposed in the form of a wound or folded hollow fiber package, wherein a transfer medium is able to flow through, and blood is able to flow around, the hollow fibers, and wherein the density of hollow fibers varies locally in the hollow fiber package in the cross-section perpendicular to length of the hollow fibers. Hollow fiber packages and methods of manufacturing thereof are provided in which the hollow fibers are held at a spacing by warp threads, in which the spacing between adjoining hollow fibers is locally increased, in particular compared to a predominantly equidistant spacing between the hollow fibers.

5 Claims, 3 Drawing Sheets

(58) Field of Classification Search
CPC .......... B01D 2313/086; B01D 2313/14; B01D 2313/143; B01D 2323/42; A61M 1/1621; A61M 1/1698

See application file for complete search history.

(56) References Cited

U.S. PATENT DOCUMENTS

| | | | |
|---|---|---|---|
| 4,950,391 A | | 8/1990 | Weickhardt |
| 5,695,702 A | * | 12/1997 | Niermeyer ............. B01D 63/02 264/129 |
| 2007/0039868 A1 | | 2/2007 | Ishibashi |
| 2010/0000939 A1 | | 1/2010 | Ishibashi |
| 2010/0155334 A1 | | 6/2010 | Taniguchi et al. |
| 2010/0224548 A1 | * | 9/2010 | Tada ...................... B01D 63/02 210/321.8 |
| 2012/0043271 A1 | * | 2/2012 | Maurer ................ B01D 63/021 210/321.9 |
| 2012/0151890 A1 | * | 6/2012 | Pearson ............... B01D 63/024 55/484 |
| 2012/0234756 A1 | * | 9/2012 | Hicks ..................... G05D 21/02 210/640 |
| 2015/0197431 A1 | | 7/2015 | Shiki |

FOREIGN PATENT DOCUMENTS

| | | | |
|---|---|---|---|
| EP | 0 329 980 A2 | | 8/1989 |
| EP | 0 862 943 A1 | | 9/1998 |
| EP | 1 674 149 A1 | | 6/2006 |
| EP | 2 042 228 A1 | | 4/2009 |
| EP | 2 153 882 A1 | | 2/2010 |
| JP | S63-168004 U | | 11/1988 |
| JP | H01176405 | * | 7/1989 |
| JP | H05-228345 A | | 9/1993 |
| JP | 2007-216175 A | | 8/2007 |

OTHER PUBLICATIONS

English language machine translation of JP2007-216175, 16 Pages, No Date.*

* cited by examiner

DEVICE FOR MASS TRANSFER, AND METHOD OF PRODUCTION

BACKGROUND OF THE INVENTION

The invention relates to a device for mass transfer between blood and a gas/gas mixture, comprising a chamber through which blood can flow and in which a plurality of mass-permeable hollow fibers are disposed in the form of a wound or folded hollow fiber package, wherein a transfer medium, and in particular a gas/gas mixture, can flow through, and the blood can flow around, the hollow fibers.

The invention also relates to a method for producing a hollow fiber package of such a device.

Devices of this type are known in the prior art and are used, for example, as oxygenators. Such devices can also be used for the purpose of purifying blood so as to remove harmful substances, for example during dialysis.

In oxygenators, such devices are used to enrich the blood flowing through the device with oxygen, and to remove carbon dioxide. This process takes place by creating a concentration gradient of the substances to be exchanged ($O_2$ and $CO_2$) between the blood and the gas/gas mixture, using the gas/gas mixture as the transfer medium flowing through the mass-permeable hollow fibers, so that the permeation process causes oxygen from the gas/gas mixture to transfer through the hollow fiber walls into the blood, and carbon dioxide from the blood to transfer through the hollow fiber walls into the gas/gas mixture. Such oxygenators can be used in heart-lung machines, for example.

Depending on the application, suitable exchange media are used to achieve purification of the blood so as to remove harmful substances, and, where necessary, enrich with other desirable substances through permeation.

Typical devices of this type have previously been produced so that at least one mat comprising a plurality of equidistantly spaced mass-permeable hollow fibers located behind one another is wound in multiple layers, and in particular is wound onto a core through which blood inflow or outflow can later take place, or so that at least one such mat is folded multiple times, forming layers. In such a mat, the hollow fibers are preferably all disposed parallel to one another, wherein the ends of the respective hollow fibers are located on opposite sides of the mat. The folding or winding can take place about a respective line parallel to the longitudinal extension directions of the fiber mats, for example.

The fibers may also be oriented in such a way that fibers of adjoining layers of the wound or folded package are at an angle other than 0° or other than 180°. For example, two or more of the mats located on top of one another can be wound or folded, wherein the fibers of different mats have an angle other than 0° or other than 180° with respect to one another.

In a respective mat, the fibers can also be disposed at an angle other than 90 degrees with respect to the extension direction of the retaining warp threads.

The aforementioned methods for production can also preferably each be used with the device according to the invention, and in particular can be refined according to the invention.

Such manners of production can yield a hollow fiber package having hollow fibers that extend at least substantially in an axial direction, which can be accommodated in a housing. Viewed in the cross-section (perpendicular to the fiber extension or perpendicular to the package extension), the hollow fiber density of the hollow fiber package is essentially the same everywhere due to the equidistance of the hollow fibers in the mat.

The process of potting, which is known in expert circles, seals the axial ends of the hollow fibers with respect to one another and with respect to a housing by way of a potting compound, in particular in centrifuges or potting systems used for this purpose.

The transfer medium, for example a gas/gas mixture, can then be conducted through the hollow fibers via the axial ends of the hollow fibers, which remain exposed, or from which the potting compound is removed after potting, and blood can be conducted between the hollow fibers, through feed ports and discharge ports provided in the housing, between the potting sites located at the axial ends. The housing walls and the potting sites form a chamber, in which the hollow fibers are disposed and through which the blood can flow, in particular without the blood making direct contact with the transfer medium, and in particular the gas/gas mixture.

Typical cylindrical devices of this type have blood inflow or outflow through a hollow core onto which the at least one mat is wound. The core, which forms a hollow channel, is open in the region of an axial end toward the chamber interior, and in particular is open to the outside in a radial direction, so that blood is able to transfer there between the core and the chamber interior. A crossover for the blood between the chamber interior and a space that is preferably disposed in the circumferential direction also takes place at the opposite axial end, preferably on the outside in a radial direction. It is essentially immaterial which of the aforementioned respective crossovers to the chamber is used as a feed port and which is used as a discharge port for the blood.

The invention preferably relates to the aforementioned design of devices, preferably comprising a radially outer blood discharge port at one of the axial ends and a radially inner blood feed port, formed by way of the winding core, at the other of the axial ends. However, the invention is not limited to these.

Within the chamber, blood generally flows through the chamber, substantially directly between the blood feed port and blood discharge port. There is less flow through regions deviating from the direct path, so that, viewed across the cross-section of a hollow fiber package perpendicular to the axial direction, the flow is irregular. This is, however, disadvantageous and, in these regions experiencing lesser flow, results in inferior mass transfer, and possibly thrombus formation.

With the aforementioned design of the device, blood thus flows substantially between the axial end regions from the radial interior, obliquely to the axial direction, to the radial exterior. Viewed across the cross-section of a hollow fiber package perpendicular to the axial direction, this results in irregular flow. The maximum flow is present in an annular region that, viewed in the radial direction, shifts from the radial interior to the radial exterior.

In general, the flow is the poorest through areas in the housing that are located opposite the inlet or the outlet of blood in the respective axial positions. Based on the specific design described, inferior through-flow thus occurs at the axial end where the crossover to the chamber is located radially inward on the hollow core, and thus at the radially outward circumferential regions of the chamber, and at the axial end where the crossover to the chamber is located radially outward, and thus at the radially inward circumferential region surrounding the core, which is closed at this axial end.

SUMMARY OF THE INVENTION

It is thus an object of the invention to equalize the flow of the blood in the chamber across the cross-section (perpendicular to the axial extension) of the hollow fiber package, which is to say increase the flow in the flow regions that are disadvantaged with the existing design.

This object is achieved in that the density of hollow fibers varies locally in the hollow fiber package, in particular viewed in the cross-section perpendicular to the hollow fiber extension or perpendicular to the package extension. Such a locally varying implementation of the hollow fiber density in the cross-section allows the flow resistance to be deliberately reduced where the hollow fiber density is reduced, for example by increasing the spacing between adjoining hollow fibers of the package. Regions that, in the prior art, were previously disadvantaged in terms of flow can thus, according to the invention, be given stronger flow by deliberately reducing the hollow fiber density there.

For this purpose, preferably at least one region having lower fiber density compared to the fiber density of surrounding regions can be disposed in the hollow fiber package. Preferably, regions are compared that, in the cross-section perpendicular to the axial extension, are each located entirely in the fiber bundle, in particular this excludes regions that extend beyond the edge region of the fiber bundle.

At least one such region having reduced fiber density may be disposed at a distance from, for example, preferably opposite, and in particular radially opposite, a blood inlet region and/or blood outlet region of the chamber.

The system can be designed so that, viewed in the cross-section, a density gradient is formed that is oriented from the region having reduced fiber density in the direction of the blood inlet and/or blood outlet, which is to say, the density in the direction of the inlet or outlet preferably increases in an axially end-side cross-sectional plane. Based on the described preferred design, an increase in density in a radial direction thus takes place at least at one axial end.

The arrangement of the density-reduced regions in relation to regions having higher fiber density may remain the same across the axial extension of a hollow fiber package, which is to say the density profile may be the same in all axial cross-sectional planes. It is preferred, however, especially with the aforementioned preferred design, that the density profile varies in different axial cross-sectional planes. In particular, as the axial position increases, a region, which is preferably an annular region, having reduced density, may shift from the radial exterior to the radial interior. This means that, for example, in an axial central position, a ring having reduced fiber density is located radially between, and in particular centrally between, annular regions having higher fiber density.

According to the invention, a region having lower fiber density may have a fiber density that is at least 5%, preferably at least 10%, and still more preferably at least 15%, lower than the fiber density in a surrounding region of the hollow fiber package, or than the highest fiber density in the hollow fiber package.

According to the invention, the fiber density may be reduced in a minority fraction of the cross-sectional surface area of the hollow fiber package, in particular at least by the aforementioned degree, compared to a majority fraction of the cross-sectional surface area, in which the fiber density is consistently higher, or at least higher within an interval. Such an interval preferably has interval boundaries having values that deviate from one another by no more than 5%.

A hollow fiber package according to the invention may be formed of at least one mat comprising a plurality of mass-permeable hollow fibers that are attached in the mat so as to be spaced apart from one another, and in particular are attached so as to be spaced apart from one another by warp threads, by way of winding or folding, wherein regions having differing densities of hollow fibers can be created, in the cross-section perpendicular to the hollow fiber extension, by influencing, and in particular establishing the spacing between the hollow fibers in the hollow fiber package, and/or in the at least one mat, so as to be locally different, before or during winding/folding.

The invention can provide that a region having lower fiber density is created by at least one hollow fiber mat that is wound or folded so as to form a hollow fiber package, in particular in which the hollow fibers are held at a spacing by warp threads, in which individual hollow fibers are removed and/or the spacing between adjoining hollow fibers is locally increased, in particular compared to a predominantly equidistant spacing between the hollow fibers. In particular, in a hollow fiber mat from which individual fibers have been removed, empty warp thread loops or stitches are thus present along the longitudinal extension of each removed fiber.

In the simplest case, hollow fiber mats of the prior art, comprising hollow fibers that are spaced apart from one another, and in particular spaced equidistantly apart from one another, can be utilized for the invention by removing individual hollow fibers therefrom.

Such a removal of individual hollow fibers can take place in selected positions from the hollow fiber mat, for example before the mat is wound or folded, which is to say before the hollow fiber package is created. The positions are preferably determined so that the density in the package is subsequently locally reduced in the desired locations, which is to say in particular in the aforementioned locations, in particular opposite, and preferably radially opposite the outlet or inlet of the blood.

The invention can also provide that, initially a hollow fiber package is wound or folded from at least one mat, in particular from at least one mat comprising hollow fibers that are spaced apart from one another, and in particular spaced equidistantly apart from one another, and that individual or multiple fibers are deliberately pulled in the desired locations, and in particular in the aforementioned locations, out of the package in the axial direction, only after the package has been formed. In particular, it again applies that empty warp thread loops or stitches are present in the package along the longitudinal extension of each removed fiber.

It is essentially possible to remove entire hollow fibers from the finished package, or from the mat in advance, without difficulty, if hollow fibers are only held at spaced apart by warp threads, but are not axially attached. In this way, it is possible to pull hollow fibers out of the looping warp threads.

The invention, however, can also provide that density variations are created in the formed package in that, in a hollow fiber mat that has not yet been wound/folded so as to form the hollow fiber package, the hollow fibers are attached at a non-equidistant spacing from one another, at least in regions, and in particular are attached regionally at a spacing from one another that is increased compared to a predominantly equidistant spacing from one another.

In an unwound mat, it is possible to provide spacings between hollow fibers, for example in different unwinding positions, that are increased, and in particular increased compared to a predominantly otherwise equidistant smaller spacing. It is also possible for the spacings between the hollow fibers to be larger in the starting region and/or the end region of a mat that has not yet been wound/folded, which is to say an unwound mat, than in an interposed region. Winding thus creates a package in which the fiber density is reduced at the radial interior and the radial exterior.

The above-described measures influence the fiber density essentially across the entire axial extension of the package in the same manner.

The invention can also provide to influence the spacing between the hollow fibers in the finished hollow fiber package by incorporating at least one placeholder between two layers of at least one hollow fiber mat during winding or folding. Such a placeholder may, for example, be wound or folded in between two layers of one and the same mat, or between two layers that are formed by two different mats.

Such a placeholder, at the site of the placeholder, thus increases the distance between the layers compared to regions in front of and behind the placeholder. The layers, or the hollow fibers thereof, preferably make contact with the placeholder at the site of the placeholder. In the case of a placeholder having a circular cross-section, the two layers are preferably each placed around the placeholder in the circumferential direction by less than 180 degrees, and in particular, in an assumed side sectional view, one layer is placed around the placeholder at the top and one at the bottom.

In opposing regions perpendicular to the axial direction of the hollow fibers/of a placeholder, the two layers are again brought together, in particular brought together without a spacing, and in particular in such a way that the layers, or the hollow fibers of the layers, make contact after being combined again. In the described opposing regions, the two layers thus transition from a state in which they each make contact with the placeholder into a state where they make contact with one another. A clear space is enclosed between these regions, which causes a reduction in density, and in particular which, in the connecting direction of the two aforementioned opposing regions, is located between the placeholder surface and the point where the layers are brought together again for the first time.

If the placeholder extends across the entire axial length of the hollow fibers, the fiber density is again influenced across the entire axial length.

However, it is also possible that one or more placeholders are only disposed in the region of the fiber ends between two layers of a folded or wound mat. In this way, in particular, a change in the fiber density toward reduced density can take place only in the region of the blood inlet or outlet regions located at the axial end.

It is also possible for a placeholder to be only disposed in the region, and in particular in the potting region, between the axial ends of the fibers between two layers, a placeholder thus not extending into the end region of the fibers.

In general, it may be provided that placeholders having a length that is less than the axial length of the hollow fibers are disposes in regions on or between the axial ends of the hollow fibers between two layers, when winding/folding at least one mat. In this way, a density reduction may take place in the hollow fiber package in essentially arbitrary locations. In particular, the density reduction takes place in an axial direction essentially across the length defined by the placeholder.

It may be provided here that such placeholders remain in the hollow fiber package. Placeholders that are accessible at the axial end may also be pulled out of the formed package before the hollow fibers are potted, wherein the hollow fibers essentially maintain the previously assumed positions thereof with respect to one another. This further frees up the space that was previously taken up by the placeholder and contributes to the local hollow fiber density reduction. When a placeholder having a circular cross-section is pulled out of the package, a free space remains in the package, which was previously taken up by the placeholder. This free space is surrounded by the two layers of the at least one hollow fiber mat in a circular segment-shaped manner, since these layers were previously seated against the outer surface of the placeholder. In general, in particular if the placeholder is not circular, the outline of the two layers also conforms to the shape of the outer surface of the removed placeholder.

Placeholders remaining in the hollow fiber package can be designed such that blood can flow therethrough, for example in that these are formed of hollow profiles, such as tubes, in particular having a perforated outer surface. If the outer surface is perforated, the perforation may be designed to form a filter surface.

Designing the at least one placeholder as a hollow profile, in particular as a tube, and preferably as a non-perforated tube, also gives the option of having a temperature control medium flow through such a placeholder. Such placeholders can serve as heat exchangers, in particular for controlling the temperature of the blood during operation. So as to achieve this, such hollow placeholders may be connected, at the respective ends thereof, to a separate fluid circuit.

In addition to the option of designing a placeholder to be hollow, the invention can also provide configuring a placeholder with a solid cross-section. Such a placeholder is thus not able to assume any further function in the bundle, beyond the placeholder function.

A placeholder, and in particular one that remains in the package, can preferably have a cross-section that is larger than the cross-section of a hollow fiber.

Preferably, the cross-section, and in particular the diameter, can be at least twice, and more preferably at least three times, as large as the cross-section of a respective hollow fiber.

This results in free spaces between the placeholder and the hollow fibers, which result in a reduction in density, in particular in the opposing outer regions of the placeholder in which the layers of the mat between which the placeholder is disposed abut one another.

In another possible embodiment, the invention can also provide that a placeholder is formed by a mass-permeable hollow fiber that participates in the mass transfer, in particular in the same manner as the remaining hollow fibers. Such a placeholder hollow fiber thus has a hollow design, has transfer medium (in particular gas) flowing through, and in particular is thus also potted at the end, and has a cross-section, and preferably a diameter, that is larger, in particular at least twice as large, and preferably at least three times as large, as the respective hollow fibers of the at least one mat. Such a hollow fiber may be separate from the hollow fibers of the mat.

In general, the hollow fibers of a mat, apart from the embodiment described hereafter, can all have the same cross-section.

The invention can also relate to a hollow fiber mat comprising hollow fibers connected by warp threads, which includes a predominant fraction of hollow fibers having a first diameter, wherein one or more hollow fibers having a second larger diameter are disposed in the mat and, likewise looped by warp threads, regionally between two such hollow fibers having the first diameter. As a result of winding or folding such a mat, a respective hollow fiber having the second larger diameter forms a placeholder around which layers of hollow fibers having the first smaller diameter extend. However, during winding or folding, these two layers are not brought together onto one another, but are brought together on the hollow fibers of the first diameter type, which are located directly adjacent to such a hollow fiber having the second diameter. Again, a hollow fiber having the second diameter can preferably have a diameter that is at least twice, and more preferably at least three times as large as a hollow fiber having the first diameter.

DETAILED DESCRIPTION OF THE INVENTION

Exemplary embodiments will be described in detail hereafter based on the figures.

Figure 1:
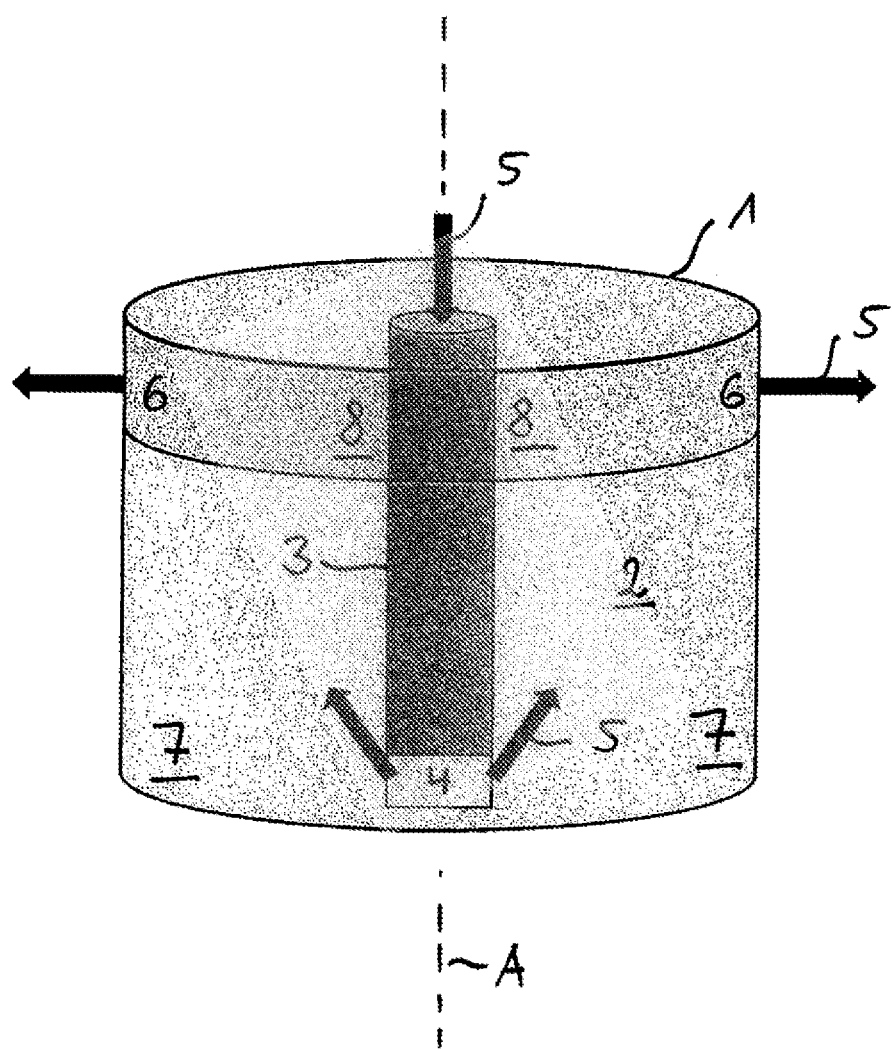
FIG. 1 shows a preferred design of a device according to the invention.

FIG. 1 shows a preferred design of a device according to the invention. The housing 1 forms a cylinder having a circular cross-section, comprising an inner chamber 2 in which mass-permeable hollow fibers, which are not shown, are disposed parallel to the axis. At the axial ends, these are supplied with a transfer medium which flows through the hollow fibers, for example a gas or a gas mixture.

The hollow fibers are disposed around the hollow channel-forming core 3, at least one mat made of such hollow fibers having been wound around the core. The core 3 has an opening 4 at the lower end here, which is thus located at the radial interior, with respect to the housing 1. The upper end of the core 3 forms the blood inlet here.

In the direction of the arrows 5, the blood admitted at the upper end of the core initially flows downward through the core, out of the opening 4 into the chamber 2, and there between the hollow fibers in the direction of the blood outlet 6, which is essentially formed in the circumferential direction and is located at the radial exterior, with respect to the housing 1.

If the hollow fiber density is at least substantially constant (viewed in a cross-section perpendicular to the axis A), the flow primarily takes place from the bottom interior to the top exterior. In the lower region, the flow through the radially exterior regions 7, which is to say those located radially opposite the opening 4 serving as an inlet for the blood into the chamber, is thus inferior. At the upper axial end, the same is true of the radially inner regions 8.

The invention ensures that the local reduction in the hollow fiber density in these regions 7 and 8 located opposite the inlet and the outlet causes the flow resistance to be reduced compared to the case in which the fiber density remains consistent across the cross-section. In this way, the flow also increases in the otherwise disadvantaged regions 7 and 8.

Figure 2:
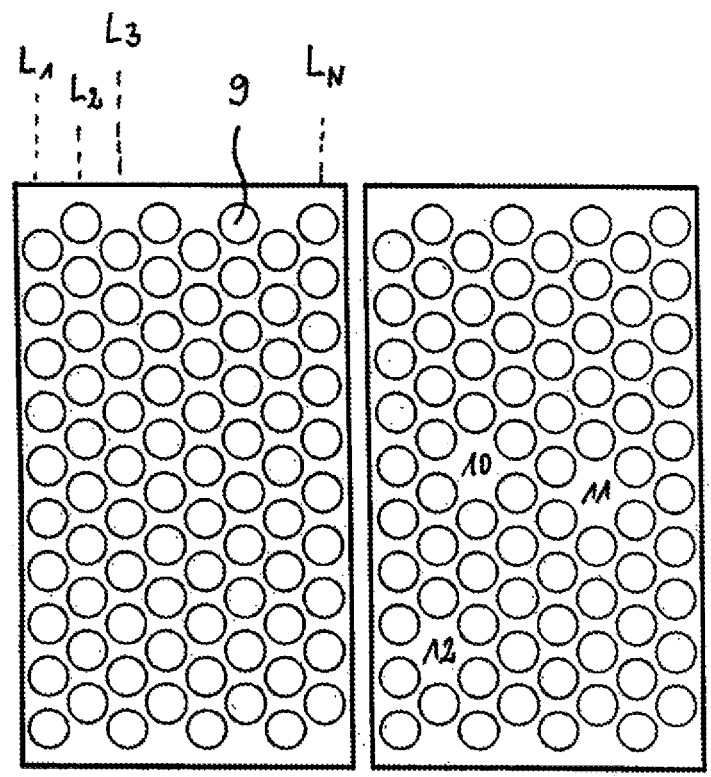
FIG. 2 shows a first embodiment for creating local fiber density reduction.

FIG. 2 shows a first option for deliberately reducing the fiber density in a desired region. On the left, FIG. 2 shows a hollow fiber package of the prior art, in which a mat comprising equidistantly spaced hollow fibers 9 in several layers L1 to Ln is wound or folded so as to form a package. Viewed across the cross-section perpendicular to the fiber extension, an overall constant fiber density is achieved in the package, at least to the extent that the fiber density is determined in a defined region that is filled entirely by fibers.

In contrast, the right of FIG. 2 shows a design according to the invention of a hollow fiber package in which individual hollow fibers were removed. This can be done in advance, in the non-wound/non-folded fiber mat, or in the finished package, by axially pulling out the desired fibers. The latter has the advantage that the position of the fibers does not have to be determined in advance. In particular, the warp thread loops of removed hollow fibers remain empty in the package.

The fiber package on the right thus includes fiber gaps 10, 11 and 12. In the region in or around these fiber gaps, it can be seen that the fiber density is thus reduced compared to the surrounding region, which is to say the flow resistance is reduced as well, and thus the flow velocity or the volume flow is increased. Such regions having reduced fiber density, which are only schematically shown here to illustrate the core idea of the invention, may be disposed where the flow would be reduced in a conventional fiber package, which is to say having a density that is otherwise the same throughout, which is to say in particular in a respective predetermined axial position opposite a blood inlet or outlet region. With respect to FIG. 1, this would be in regions 7 and 8, for example.

Figure 3:
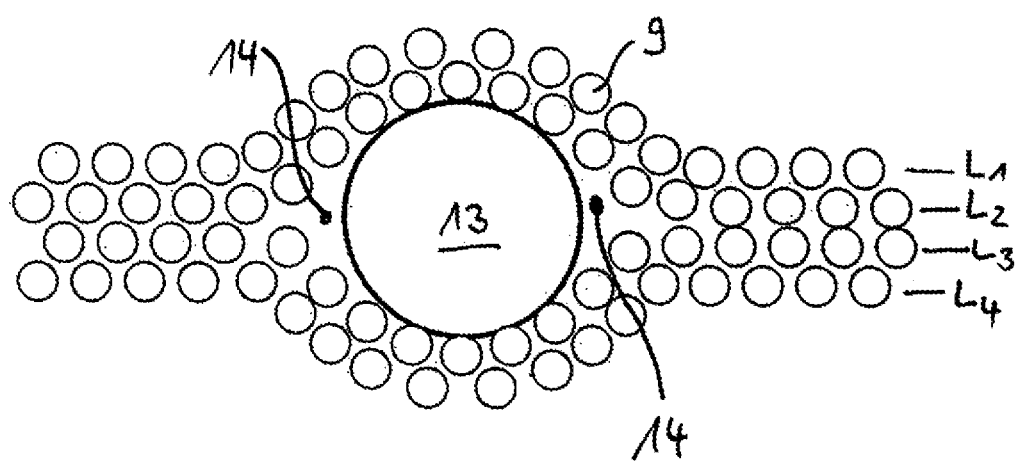
FIG. 3 shows a second embodiment for creating local fiber density reduction.

FIG. 3 shows an alternative method for creating local fiber density reduction. A section of a hollow fiber package formed according to the invention, comprising multiple wound or folded layers L1 to L4, is shown.

A placeholder 13 is disposed between the layers L2 and L3 and can either extend across the entire axial length of the hollow fibers or have a shorter length than a respective hollow fiber and may then, for example, be disposed somewhere between the axial ends of the hollow fibers, for example in a region at the axial end.

In this embodiment, the placeholder 13 has a cross-section that is larger than the cross-section of each fiber 9. Free spaces are created in opposing regions 14 of the placeholder 13 where the layers L2 and L3 lift off the placeholder and are brought together again, resulting in the desired density reduction. The placeholder itself can also contribute, through its own volume, to the density reduction, when blood can flow therethrough, for which purposes the placeholder can be designed as a perforated tube. However, the placeholder can also be designed to have a solid cross-section, so that only the regions 14 have a density-reducing effect. According to the above embodiments, however, this placeholder 13 itself can also form a mass-permeable hollow fiber, which participates in the mass transfer.

Such placeholders can be disposed, for example, based on FIG. 1, in the region 8, which is to say at the top and radial interior, and in the region 7, which is to say at the bottom and radial exterior, so as to favor the flow there locally.

If the placeholders are accessible at the axial end in the wound/folded package, these may be removed from the package prior to the fibers being potted. If these remain, they are preferably also surrounded by the potting compound.

Figure 4:
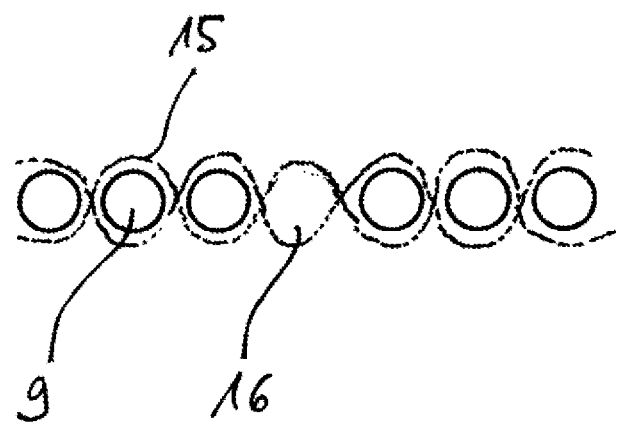
FIG. 4 shows a third embodiment for creating local fiber density reduction.

FIG. 4 shows one of the options for causing a density reduction by way of the hollow fiber mat. A section of a mat comprising hollow fibers 9 is shown, in which the hollow fibers 9 are all equidistant and are kept at a spacing by warp threads 15. The warp threads achieve stable bonding of the mat here. In this example, one of the hollow fibers has been pulled out of such a mat, by way of example, whereby the empty loop/stitch 16 of the warp threads 15 remains at this site. During winding or folding, this loop causes a reduction in density, as is essentially shown in FIG. 2. It is also possible, of course, for hollow fibers to be removed in several positions, including in consecutive positions, in such a mat.

Figure 5:
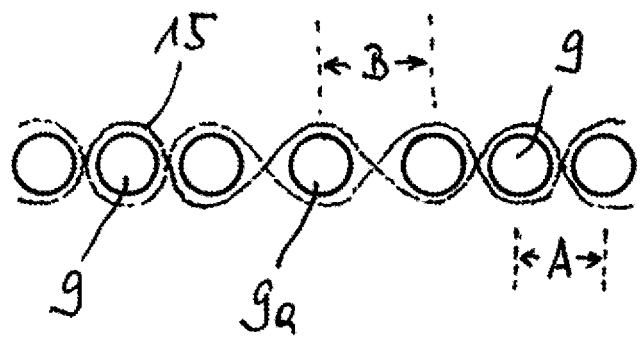
FIG. 5 shows a fourth embodiment for creating local fiber density reduction.

FIG. 5 illustrates another embodiment according to the invention of a mat of such hollow fibers 9, which are predominantly held at an equidistant spacing A in the mat by the warp threads 15. In contrast, a minority of hollow fibers, and only one hollow fiber 9a in the section here, has an increased spacing in the mat, and in particular an increased spacing with respect to adjoining hollow fibers. This increased spacing B is implemented by an increased spacing between the loop/stitch centers of the warp thread pair of this hollow fiber 9a compared to that of the other hollow fibers 9.

Figure 6:
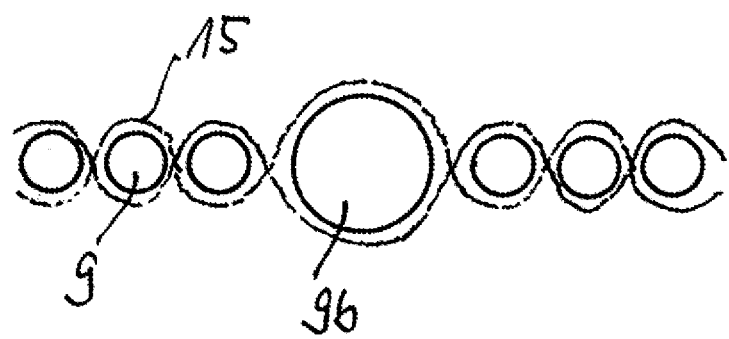
FIG. 6 shows a sixth embodiment for creating local fiber density reduction.

FIG. 6 shows one embodiment in which a minority of hollow fibers, constituted by one mass-permeable hollow fiber 9b in the section here, has a larger diameter than the other hollow fibers 9 constituting the majority of all the hollow fibers in the mat. As a result of being looped by the warp threads 15, this hollow fiber 9b is part of the mat in the same manner as all the other hollow fibers 9. During winding/folding, the desired density reduction is achieved in the surrounding area of the hollow fiber 9a in a manner similar to that described for a placeholder 13 in FIG. 1, with the difference that layers (not shown here), which are placed around the hollow fiber 9b during folding/winding, are not placed on top of one another in laterally opposing positions next to this hollow fiber 9b, but are placed on the hollow fiber 9 to the right and left next to the hollow fiber 9b.

The invention claimed is:

1. A device for mass transfer between blood and a gas/gas mixture, comprising a chamber configured for flow of blood therethrough and in which hollow fibers which are mass-permeable, are connected by and held at a spacing from one another by warp threads and are disposed in a form of a wound or folded hollow fiber package configured as layers of the hollow fibers which are connected by and held at a spacing from one another by warp threads, and the device being configured so that a transfer medium is able to flow through, and blood is able to flow around, the hollow fibers, wherein density of hollow fibers varies locally in the hollow fiber package within individual cross-sections of the entire hollow fiber package perpendicular to length of the hollow fibers and independently of any varying of area of the cross-sections of the entire hollow fiber package perpendicular to length of the hollow fibers so that the hollow fiber package has at least one region of lower hollow fiber density than another region, and wherein said at least one region of lower hollow fiber density comprises at least one placeholder inserted into the hollow fiber package at least at an axial end of the hollow fiber package and interposed between two mutually adjacent hollow fiber layers of the hollow fiber layers of the hollow fiber package, the placeholder being separate from and not being connected to the hollow fibers of the hollow fiber package by the warp threads.

2. The device according to claim 1, wherein the placeholder has a cross-section larger than the hollow fibers of the two layers.

3. The device according to claim 1, wherein a region having lower hollow fiber density is disposed radially opposite at least one of a blood inlet region and a blood outlet region of the chamber.

4. A device for mass transfer between blood and a gas/gas mixture, comprising a chamber configured for flow of blood therethrough and in which hollow fibers which are mass-permeable, are held at a spacing from one another by warp threads and are disposed in a form of a wound or folded hollow fiber package, and the device being configured so that a transfer medium is able to flow through, and blood is able to flow around, the hollow fibers, wherein density of hollow fibers varies locally in the hollow fiber package within individual cross-sections perpendicular to length of the hollow fibers and independently of area of the cross-sections so that the hollow fiber package has at least one region of lower hollow fiber density than another region, wherein said at least one region of lower hollow fiber density comprises at least one placeholder inserted into the hollow fiber package at least at an axial end of the hollow fiber package and interposed between two mutually adjacent layers of the hollow fibers connected by warp threads, the placeholder being separate from the hollow fibers of the hollow fiber package and wherein at least one of the placeholders is in the form of a mass-permeable hollow fiber that has a diameter that is larger than the majority of the other mass-permeable hollow fibers.

5. The device according to claim 4, wherein the placeholder is not connected to the hollow fibers of the hollow fiber package by the warp threads.

* * * * *